(12) United States Patent
Kambourakis et al.

(10) Patent No.: US 10,087,161 B2
(45) Date of Patent: Oct. 2, 2018

(54) SYNTHESIS OF FDCA AND FDCA PRECURSORS FROM GLUCONIC ACID DERIVATIVES

(71) Applicant: Synthetic Genomics, Inc., La Jolla, CA (US)

(72) Inventors: Spiros Kambourakis, San Diego, CA (US); Benjamin M. Griffin, San Diego, CA (US)

(73) Assignee: Synthetic Genomics, Inc., La Jolla, CA (US)

( * ) Notice: Subject to any disclaimer, the term of this patent is extended or adjusted under 35 U.S.C. 154(b) by 0 days.

(21) Appl. No.: 15/202,298

(22) Filed: Jul. 5, 2016

(65) Prior Publication Data

US 2017/0050944 A1    Feb. 23, 2017

Related U.S. Application Data

(60) Provisional application No. 62/207,838, filed on Aug. 20, 2015.

(51) Int. Cl.
*C07D 307/46* (2006.01)
*C07D 307/40* (2006.01)
*C07D 307/68* (2006.01)
*C12P 17/04* (2006.01)
*C12P 7/58* (2006.01)

(52) U.S. Cl.
CPC .............. *C07D 307/68* (2013.01); *C12P 7/58* (2013.01); *C12P 17/04* (2013.01)

(58) Field of Classification Search
CPC ............................ C07D 307/46; C07D 307/40

USPC .................................................. 549/484, 485
See application file for complete search history.

(56) References Cited

U.S. PATENT DOCUMENTS

2013/0296451 A1    11/2013   Abraham et al.
2014/0106414 A1    4/2014    Kambourakis et al.

FOREIGN PATENT DOCUMENTS

WO    WO 2016/141148 A1 *    9/2016    ............ C07D 307/44

OTHER PUBLICATIONS

Chatterjee et al.: "*Chemical Conversion Pathways for Carbohydrates*"; Green Chemistry, 2015, vol. 17, Issue 1, pp. 40-77.
International Search Report dated Sep. 23, 2016, regarding PCT/US2016/040983.

* cited by examiner

*Primary Examiner* — Charanjit Aulakh
(74) *Attorney, Agent, or Firm* — DLA Piper LLP (US)

(57) ABSTRACT

The present invention provides methods of method of synthesizing 2,5-furan dicarboxylic acid (FDCA) and FDCA precursor molecules. The methods involve performing a chemical dehydration reaction on a gluconic acid derivative in the presence of a dehydration catalyst. In some embodiments the gluconic acid derivative can be 2-dehydro-3-deoxy gluconic acid (DHG) or an ester thereof, 2-ketogluconic acid (2KGA) or an ester thereof, and 5-ketogluconic acid (5KGA) or an ester thereof. The 2,5-furan dicarboxylic acid precursor molecule is thereby synthesized, which can be converted into FDCA. The chemical dehydration can be performed by a variety of acid basic catalysts.

25 Claims, 9 Drawing Sheets

SYNTHESIS OF FDCA AND FDCA PRECURSORS FROM GLUCONIC ACID DERIVATIVES

This application claims the benefit of U.S. provisional application Ser. No. 62/207,838, filed Aug. 20, 2015, which is incorporated by reference herein in its entirety, including all Tables, Figures, and claims.

FIELD OF THE INVENTION

The invention pertains to the synthesis of FDCA and FDCA precursors from derivatives of gluconic acid.

BACKGROUND OF THE INVENTION

In recent years, an increasing effort has been devoted to identify new and effective ways to use renewable feedstocks for the production of organic chemicals. Among a plethora of downstream chemical processing technologies, the conversion of biomass-derived sugars to value-added chemicals is considered very important. In particular, six-carboned carbohydrates, i.e. hexoses such as fructose and glucose, are widely recognized the most abundant monosaccharides existing in nature, therefore can be suitably and economically used as the chemical feedstocks.

The production of furans and furan derivatives from sugars has attracted increasing attention in chemistry and in catalysis studies, and is believed to have the potential to provide one of the major routes to achieving a sustainable energy supply and source of chemicals production. Indeed, dehydration and/or oxidation of the sugars available within biorefineries with integrated biomass conversion processes can lead to a large family of products including a wide range of furans and furan derivatives.

Among the furans having the most commercial values, furan-2,5-dicarboxylic acid (also known as 2,5-furandicarboxylic acid, hereinafter abbreviated as FDCA) is a valuable intermediate with various uses in several industries including pharmaceuticals, pesticides, antibacterial agents, fragrances, agricultural chemicals, as well as in a wide range of manufacturing applications of polymer materials, e.g. bioplastic resins. As such, FDCA is considered a green alternative of terephthalic acid (TA), a petroleum-based monomer that is one of the largest-volume petrochemicals produced yearly worldwide. In fact, the US Department of Energy has identified FDCA as one of the top 12 priority compounds made from sugars into a value-added chemical for establishing the "green" chemistry of the future, and as such, it has been named one of the "sleeping giants" of the renewable intermediate chemicals (Werpy and Petersen, *Top Value Added Chemicals from Biomass*. US Department of Energy, Biomass, Vall, 2004).

Although various methods have been proposed for commercial scale production of FDCA (for review, see, e.g., Tong et al., *Appl. Catalysis A: General*, 385, 1-13, 2010), present methods of synthesizing FDCA rely on the chemical dehydration of hexoses, such as glucose or fructose, to the intermediate 5-hydroxymethylfurfural (5-HMF), followed by a chemical oxidation to FDCA. During this oxidation HFCA (2-hydroxymethyl 5-furan carboxylic acid), or FFCA (2-formyl-5-furan carboxylic acid) are produced as transient intermediates (van Putten, R-J et al., *Chem Rev.* 2013, 113(3), 1499-1597). However, current FDCA synthesis processes via dehydration of fructose have many drawbacks. For example, fructose is produced from the enzymatic isomerization of glucose, and as a result, a mixture of glucose and fructose is produced, requiring fructose to be separated before chemical dehydration. Furthermore, the high degree of freedom of the fructose molecule produces a number of other byproducts and, as a result, optimizing its dehydration to produce HMF in high yields remains challenging (especially when inexpensive conditions amenable to scale up are required). Thus, the primary technical barrier in the production and use of FDCA is the development of an effective and selective dehydration process from biomass-derived sugars.

Other chemicals exist that can be obtained from the conversion of glucose, by either chemical or enzymatic means, such as 2-ketogluconate, 5-ketogluconate, or 2-dehydro-3-deoxygluconate (DHG). But there are no methods available for the efficient conversion of these compounds into 2-formyl-5-furan carboxylic acid (FFCA) or 3-dehydro-5-furan carboxylic acid (HFCA), or further into the more valuable 2,5-furan dicarboxylic acid (FDCA).

It is therefore desirable to develop methods for production of FDCA and FDCA precursors, as well as many other chemicals and metabolites, by alternative means that not only would allow for the substitution of renewable feedstocks for petroleum-based feedstocks, but also use less energy and capital-intensive technologies. In particular, intermediate processes for transforming abundant sugars into precursors that could be readily converted into FDCA would be a very powerful technology, leading to inexpensive production of this valuable chemical as well as other carboxylic acids.

SUMMARY OF THE INVENTION

The present invention provides methods of synthesizing 2,5-furan dicarboxylic acid (FDCA) and FDCA precursor molecules. The methods involve performing a chemical dehydration reaction on a gluconic acid derivative, which in some embodiments can be 2-dehydro-3-deoxy gluconic acid (DHG) or an ester thereof, 2-ketogluconic acid (2KGA) or an ester thereof, and 5-ketogluconic acid (5KGA) or an ester thereof. The 2,5-furan dicarboxylic acid precursor molecule is thereby synthesized. The chemical dehydration can be performed in the presence of an acid catalyst or a basic catalyst. In some embodiments the FDCA precursor is 2-hydroxymethyl-5-furan carboxylic acid (HFCA) or 2-formyl-5-furan carboxylic acid (FFCA). The FDCA precursor can, optionally, be converted into FDCA through an oxidation reaction.

In a first aspect the invention provides methods of synthesizing a 2,5-furan dicarboxylic acid (FDCA) precursor molecule. The methods involve performing a chemical dehydration reaction on 2-dehydro-3-deoxy gluconic acid (DHG) or an ester thereof, 2-ketogluconic acid (2KGA) or an ester thereof, or 5-ketogluconic acid (5KGA) or an ester thereof, in the presence of a dehydration catalyst to thereby synthesize the 2,5-furan dicarboxylic acid precursor molecule. In some embodiments the dehydration catalyst is an acid catalyst, for example a mineral acid (e.g., $H_2SO_4$, HCl, $HClO_4$, HBr, $Nb_2O_5$, and $H_3PO_4$). In some embodiments the dehydration catalyst is an immobilized catalyst, which can be polymeric material, or a copolymer of polystyrene and divinylbenzene, or zeolite. In one embodiment the immobilized catalyst is a sulfonic group on polystyrene. The chemical dehydration can occur at a temperature of from 20° C. to about 150° C. The FDCA precursor can, for example, 2-formyl-5-furan carboxylic acid (FFCA), or 2-hydroxymethyl-5-furan carboxylic acid (HFCA), or an ester of any of them. The reaction can be performed in a solvent such as, for example, acetic acid and water, or a mixture of acetic acid and water, or a mixture of an alcohol and water. In various embodiments the acid catalyst can be $H_2SO_4$, HCl, HBr, $H_3PO_4$, an immobilized acid comprising a sulfonic group on polystyrene, or an immobilized acid comprising a copolymer of polystyrene and divinylbenzene.

In some embodiments the FDCA precursor (e.g., HFCA or FFCA) is converted into 2,5-furan dicarboxylic acid (FDCA), which can involve oxidation of the HFCA or FFCA. The oxidation can occur under acidic conditions. The oxidation can also occur in the same solvent as the dehydration. In some embodiments the method does not comprise a step of purifying the HFCA or FFCA. In various embodiments oxidation can occur in the presence of peroxide or oxygen and, optionally, in the presence of an oxidation catalyst, for example $CoNO_3/MnNO_3$, PVC, Pt—Ru/C, Pd/C, or Pt—Ru/C.

In some embodiments of the dehydration reaction the dehydration catalyst is a basic catalyst, for example $Na_2CO_3$, NaOH, and KOH. The reaction can be performed in various solvents, for example acetic acid and water, or a mixture of acetic acid and water. The FDCA precursor can be converted into 2,5-furan dicarboxylic acid (FDCA) through oxidation of the precursor. Any of the chemical dehydration reactions described herein can occur at a temperature of from 20° C. to about 150° C.

In another aspect the invention provides methods for the synthesis of an FDCA precursor involving oxidizing glucose into gluconic acid; enzymatically oxidizing the gluconic acid into a 2- or 5-keto-gluconic acid; performing a dehydration reaction to convert the 2- or 5-keto-gluconic acid into an FDCA precursor (e.g. FFCA). The oxidation of the glucose and the oxidation of the gluconic acid can be performed in a cell culture. The cell culture can contain an acetic acid bacteria, for example *Acetobacter, Gluconobacter, Gluconoacetobacter.*

In another aspect the invention provides methods for the synthesis of an FDCA precursor involving oxidizing glucose into gluconic acid; enzymatically dehydrating the gluconic acid into dehydro-gluconic acid (DHG); performing a dehydration reaction to convert the DHG into an FDCA precursor (e.g., HFCA). The oxidation of the glucose and the dehydration of the gluconic acid can be performed in a cell culture, and the cell culture can contain an acetic acid bacteria, for example *Acetobacter, Gluconobacter, Gluconoacetobacter.*

DESCRIPTION OF THE DRAWINGS

FIGS. 5A-D show NMR spectra for the dehydration of 5KGA in a Dean Stark apparatus (all samples dissolved in DMSO with an internal standard).

DETAILED DESCRIPTION OF THE INVENTION

The invention provides methods of synthesizing carboxylic acids from a gluconic acid derivative. In particular embodiments the invention can be used to synthesize FDCA precursors, such as 2-hydroxymethyl-5-furan carboxylic acid (HFCA) or an ester thereof, and 2-formyl-5-furan carboxylic acid (FFCA) or an ester thereof, through the dehydration of 2-ketogluconate (2KGA) or 5-ketogluconate (5KGA) or 2-hydro-3-deoxy gluconate (DHG), or an ester of any of them. FFCA and HFCA and other precursors can then be used to synthesize the highly valuable chemical 2,5-furan dicarboxylic acid (FDCA) or derivatives thereof.

Figure 1:
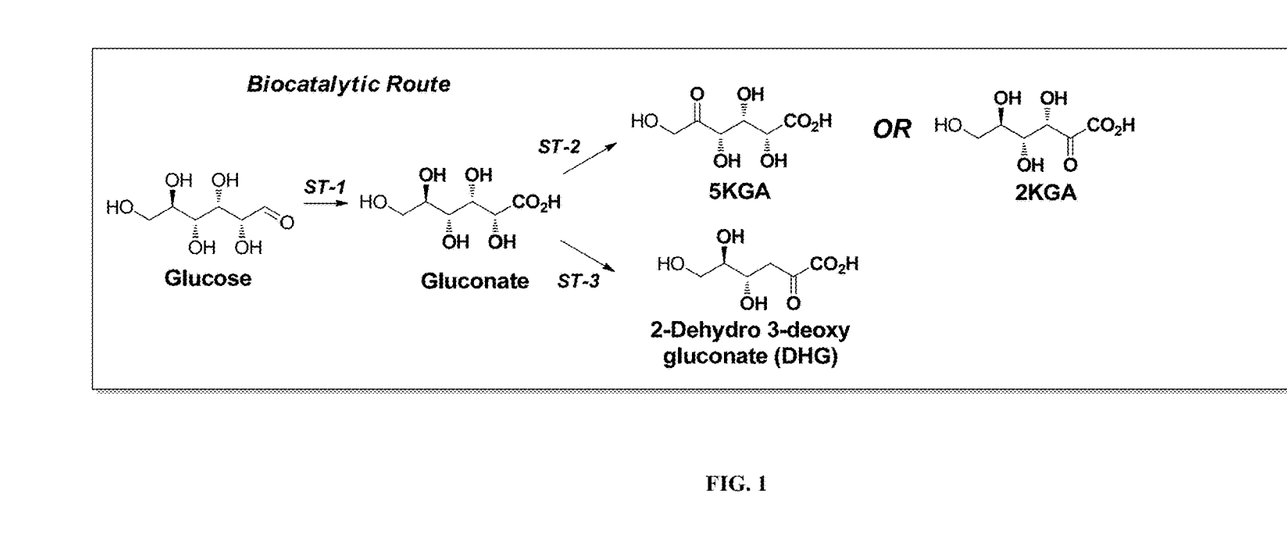
FIG. 1 provides a biocatalytic route for synthesizing gluconic acid and gluconic acid derivatives.

The invention provides many significant advantages. The substrate molecules used in the present invention, for example 2KGA, 5KGA, DHG, or a derivative of any of them can be readily obtained from commercial sources or from the enzymatic oxidation of glucose such as described herein and, in the case of DHG, an additional dehydration (FIG. 1). Such reactions can be conveniently and efficiently performed in cell free biocatalytic reactions using purified enzymes, semi-purified lysates, or crude lysates of bacteria or yeast, that desirably can be recombinantly engineered to over-express the necessary genes to perform such conversions. Furthermore, various microorganisms (e.g., acetic acid bacteria) can very efficiently oxidize glucose to either of gluconate, 5KGA, or 2KGA, or mixtures (Saichana, N. et al., *Biotechnol. Adv.*, 2015, 33(6), 1260; Elfari, M. et al. *Appl. Microbiol. Biotechnol.* 2005, 66, 668). Synthesis of 2-dehydro-3-deoxygluconate (or dehydrogluconate) (DHG) can be performed by the action of gluconate dehydratase (EC 4.2.1.39) under cell-free conditions (e.g., by an immobilized enzyme on a solid support) or in whole cell fermentations where the gene is expressed in a gluconate-producing organism (e.g. acetic acid bacteria, yeast, etc).

The methods of the invention allow for the efficient synthesis of precursors of 2,5-furan dicarboxylic acid (e.g., HFCA, FFCA, FFCA-diketal, or an ester of any). In some embodiments the FDCA precursors are also furans or contain a furan ring. The FDCA precursors are synthesized through the dehydration of gluconic acid derivatives such as, for example, 2KGA, 5KGA, and DHG, or a carboxylic acid ester of a gluconic acid derivative. The FDCA precursors can optionally be converted into FDCA.

While existing methods require careful and selective oxidation conditions to achieve the desired product and often result in significant quantities of unwanted products, the present methods have the advantage of eliminating these problems because DHG, or 5KGA or 2KGA or the ester of any of them, are already oxidized to the carboxylic acid (or corresponding ester) prior to the dehydration, and therefore many unwanted products do not have an opportunity to form. The methods of the invention also do not require the isomerization of fructose nor the use of any isomerase.

Methods

Figure 2:
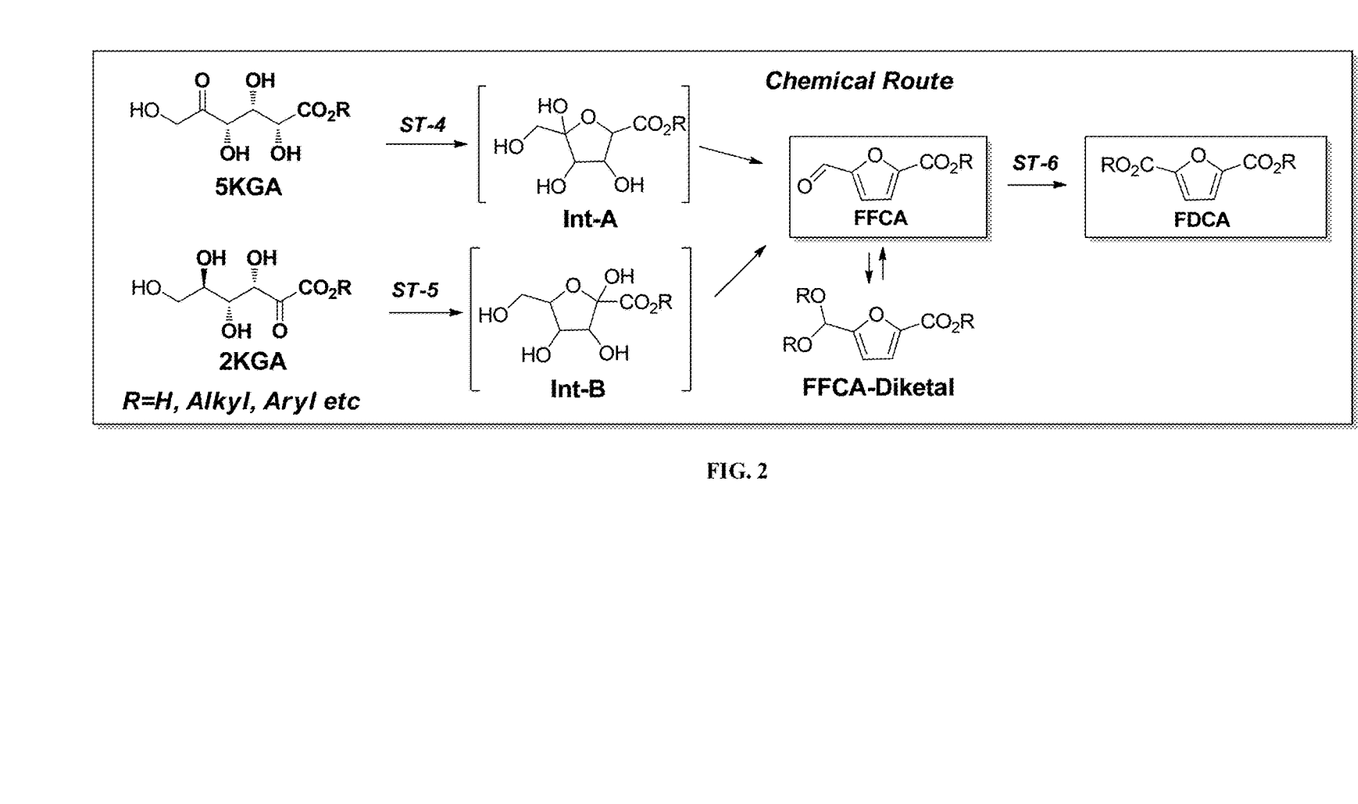
FIG. 2 provides a scheme showing pathways for synthesizing an FDCA precursor (in this embodiment FFCA) and FDCA from 2KGA or 5KGA using reactions of the invention.
Figure 3:
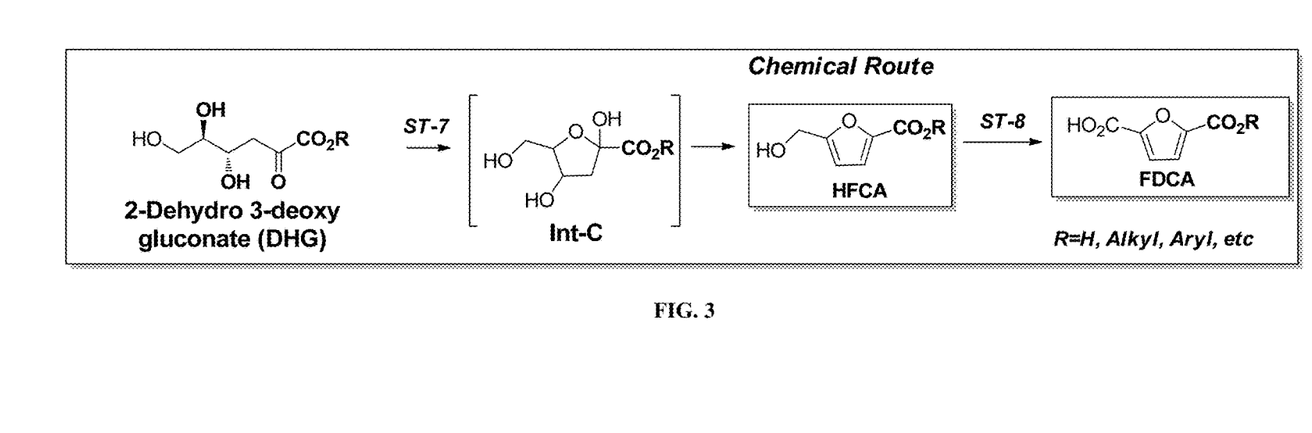
FIG. 3 provides a scheme showing pathways for synthesizing an FDCA precursor (in this embodiment HFCA) and FDCA from DHG using reactions of the invention FIG. 4 provides a reproduction of a UV-illuminated TLC plate of 5KGA dehydration samples. Running buffer was 85/15 v/v hexane/ethyl-acetate). Lanes, reading left to right, are 1 h, 3 h (TLC of crude reaction samples from 1 h and 3 h); F (reaction sample after incubation in water); and P1, P2 (purified compounds B and A, respectively, using flash chromatography).

One step in the methods of the invention is a dehydration step of a gluconic acid derivative (or its ester) to produce an FDCA precursor molecule (or its corresponding ester). Aspects of the invention discussed herein that relate to the free acid form of a gluconic acid derivative or FDCA precursor are also applicable and set forth with respect to the corresponding esters. Dehydration reactions generally involve the loss of a water molecule from a reacting molecule. In some embodiments the dehydration of 5KGA, 2KGA, and DHG may proceed through the intermediates A, B, or C, respectively (FIGS. 2 and 3). The later intermediates may then lose three (5KGA, 2KGA) or two (DHG) water molecules to produce FFCA and HFCA, respectively. If the dehydration of 5KGA and 2KGA is performed in an alcohol (e.g., MeOH, EtOH, BuOH, and the like) an additional furan diketal intermediate (FFCA-diketal) can also be formed as shown in FIG. 2, which can have one or more esters of the alcohol. The later molecule is in equilibrium with the aldehyde in alcoholic solvents and quickly hydrolyzes to the aldehyde when incubated in water. Thus, in one embodiment the reaction of the invention can involve a pathway that creates one or more diketal intermediates, which can optionally contain one or more alkyl ester groups.

The dehydration reactions or steps of the invention can be performed by various means. Generally the reactions can be performed in any appropriate container, such as a vial, test tube, a stirred glass or steel reactor, a batch reactor, continuous flow reactor, a Dean Stark apparatus, distilling trap, or Dean Stark head, or other appropriate container. But in various embodiments the reactions can be performed either in batch reactors (or batch production) or in continuous flow reactors. The reactions can be performed in the presence of immobilized dehydration catalysts.

A batch reactor is simply a vessel in which a reaction is performed. In some embodiments it can have an agitator to promote mixing and the reaction. In a batch reaction the reaction components are generally added to the vessel and the reaction then occurs in the vessel, at which point the product is retrieved. Generally in batch production the solvent can be added to the container with a gluconic acid derivative, which can then be partially or completely dissolved in the solvent. The acid or base catalyst can then be added and the reaction incubated at an appropriate temperature and for an appropriate time period with (or without) stirring.

In other embodiments the dehydration reaction can take place in a continuous flow reactor (i.e. by flow chemistry). Generally, in these reactions the substrate 5KGA, 2KGA or DHG free acids or esters are moved through tubes and the tubes carrying reactants join one another and then pass over the column that contains the dehydration catalyst.

In another embodiment the reactants can be pre-mixed (a pre-mixed continuous reaction) where the substrate(s) are dissolved in water or in an organic or aqueous mixed solvent or other solvent as described herein and are mixed together prior to being passed through the column containing a solid phase, immobilized dehydration catalyst. In some embodiments an acid (e.g., a Bronsted acid such as HCl, HBr, $H_2SO_4$ etc., or a Lewis acid such as $AlCl_3$, $BF_3$, etc.) is also be included and the mixture then passed through the continuous reactor column containing the catalyst. This reactor can also contain an inert material such as sand or an immobilized acid on a polymer or resin as described herein.

Under any of these continuous flow conditions the dehydrated products (e.g., FFCA, HFCA, FFCA-diketal or their esters (such as $C_{1-3}$ or $C_{1-4}$ straight or branched chain carboxylic acids) are in contact with the catalyst only for a short amount of time (depending on the flow rate and reactor size) and are continuously removed from the catalyst. This can advantageously minimize byproduct formation and increase product yield.

In any type of production the reactions can proceed for an appropriate period of time such as, for example about 10 minutes or about 20 minutes or about 30 minutes or at least 10 minutes or at least 20 minutes or at least 30 minutes or 10-20 minutes or 10-30 minutes or 10-60 minutes or at least 1 hour or at least 2 hours or at least 3 hours or at least 4 hours or at least 10 hours or at least 12 hours or at least 20 hours or at least 30 hours or about 40 hours or 1-3 hours or 1-10 hours or 1-30 hours or 2-30 hours or 2-20 hours or 4-15 hours or 5-10 hours.

In any of the above types of reactions heat can be applied and an advantageous temperature can be easily determined. The dehydration reactions or steps, and the oxidation reactions or steps, described herein can be performed at a very wide range of temperatures including, but not limited to, 20-150° C., or 10-170° C. or 20-30° C. or 20-40° C. or 20-50° C. or 20-100° C. or 20-125° C. or 30-50° C. or 30-150° C. or 30-170° C. or 30-70° C. or 30-120° C. or 50-100° C. or 50-125° C. or 70-80° C. or 70-130° C. or 70-150° C. or 60-140° C. or 80-100° C. or 80-120° C. or 100-150° C. or greater than 80° C. or greater than 90° C. or greater than 100° C. or greater than 110° C. or about 110-130° C. or about 30° C. or about 40° C. or about 50° C. or about 75° C. or about 100° C. or about 120° C. or about 150° C.

The reactions can be carried out on either the free acid form of the gluconic acid derivatives or on the esterified forms, as described herein. Persons of ordinary skill will understand that when the ester form is utilized then the corresponding ester of the FDCA precursor can be produced or the free acid of the FDCA precursor, depending on the reaction conditions and solvent used. Thus, if the methyl ester form of DHG is utilized as a gluconic acid derivative then the methyl ester form of HFCA can be produced by the reaction under appropriate circumstances. Whether the free acid or ester of the FDCA precursor is produced can also depend on the solvent used. A mixed solvent could produce a mixture of esters or a mixture of one or more esters and the free acid form. Similarly, the esterified form of the gluconic acid derivative can be used but, depending on the conditions, the free acid form of the FDCA precursor can be produced.

The methods can also involve one or more optional extraction step(s) after formation of the FDCA precursor. Extractions can be done in any appropriate solvent depending on what chemical is being extracted, such as an organic solvent. When multiple extractions are done they can be done with the same or with a different extraction solvent. Examples of appropriate extractions solvents include, but are not limited to, water and saturated sodium chloride, non-miscible aqueous solvents such as ethers (e.g. diethyl, propyl, iso-propyl, butyl, iso-butyl, tert-butyl-methyl, etc.), esters (e.g., ethyl acetate, propyl acetate, butyl acetate, etc.), and alkanes (e.g. hexane, petroleum ether, $C_3$-$C_8$ or $C_4$-$C_6$ linear or cyclic alkanes).

In some embodiments the dehydration step in the methods is performed by a chemical dehydration, meaning that the dehydration step does not involve or require the action of an enzyme. Instead the reaction can proceed as a chemical dehydration reaction and does not involve or require the action of an enzyme as a cofactor. In other embodiments the entire method of synthesizing FDCA from DHG, 2KGA, or 5KGA is chemical or non-enzymatic, meaning that the entire synthesis proceeds as a chemical synthesis and does not involve or require the action of an enzyme as a cofactor or otherwise. In other embodiments the dehydration step and or the method of synthesizing FDCA from DHG, 2KGA, or 5KGA can be performed enzymatically or through a combination of chemical and enzyme mediated reactions.

In some embodiments the method can be a bio-based method for the synthesis of a precursor of FDCA. The method involves oxidation of glucose into gluconic acid and the enzymatic oxidation of the gluconic acid into ketogluconic acid (e.g. 2KGA or 5KGA). This can be followed by a dehydration reaction into an FDCA precursor (e.g., FFCA). In some embodiments the oxidation can be performed on a recombinant cell, which can be grown in a fermenter or cell culture. The recombinant cells can be bacterial (e.g. acetic acid bacteria such as *Acetobacter, Gluconobacter, Gluconoacetobacter*) or yeast cells. In some embodiments the gluconic acid can be enzymatically dehydrated into DHG, which can then be dehydrated into an FDCA precursor (e.g. HFCA) as described herein.

Gluconic Acid Derivatives

The term gluconic acid derivative refers to molecules that have the basic backbone structure of a gluconic acid derivative, which can have the molecular formula $C_6O_{6-7}H_{9-10}$ and the condensed structural formula $HO(CH_2)(CO)(CHOH)_3(COO^-)$ or $HO(CH_2)(CHOH)_2(CH_2)(CO)(COO^-)$, and can also have one or more ester groups, when present. In certain embodiments the dehydrogenation or dehydration of gluconic acid produces a gluconic acid derivative. Examples of gluconic acid derivatives include, but are not limited to, 2-dehydro-3-deoxy gluconic acid (DHG), 2-ketogluconate (2KGA), and 5-ketogluconate (5KGA), and esters of any of them. An ester of any of these molecules is also considered a gluconic acid derivative.

As used herein an ester can be, but is not limited to, carboxylic acid esters. Examples of esters include, but are not limited to, an alkyl ester, a methyl ester, ethyl esters, propyl esters, isopropyl ester, butyl esters, isobutyl esters, sec-butyl esters, tert-butyl esters, an ester of a $C_{1-4}$ alkane or alkene, $C_{1-5}$ alkane or alkene, or a $C_{1-6}$ alkane or alkene, $C_{1-7}$ alkane or alkene, or a $C_{1-8}$ alkane or alkene, any of which can be a straight or branched chain alkane or alkene. The ester can also be of a cyclic alkane or alkene.

In embodiments where esters are utilized in the reaction an ester forming catalyst can be added to the reaction such as, for example, chloride derivatized silica but any esterification catalyst can be used. This can be done either together with the dehydration catalyst or in a separate esterification reaction where the 5KGA, 2KGA, or DHG ester (or ester of another gluconic acid derivative) is made prior to the dehydration, as described earlier. Some non-limiting of esterification catalysts include p-toluenesulfonic acid and $H_2SO_4$.

FDCA Precursors

An FDCA precursor is a molecule that can be readily converted into FDCA. In some embodiments the FDCA precursor has a furan group and a carboxylic acid (or one or more esters, which can be one or more carboxylic acid ester(s)). In some embodiments the FDCA precursor can be converted into FDCA in a single step, which can be a chemical conversion step. But in some embodiments the FDCA precursor can also be converted into FDCA in more than one step, or in two steps, or in more than two steps, or within three steps. In another embodiment the FDCA precursor can be converted into FDCA through a transient intermediate, which is considered one step.

A chemical conversion step relies on chemical reactants to complete the step and does not require an enzyme as cofactor or enzymatic conversion. The single step encompasses situations where an equilibrium exists between two molecules and one of the molecules is converted into FDCA. Thus, a molecule that is in equilibrium with a second molecule that is converted into FDCA to an extent that it drives a significant reaction can be considered an FDCA precursor. In some embodiments the FDCA precursor is not a transient intermediate, but is a stable molecule. A stable molecule can be one that can be stored in ordinary laboratory conditions for 1 hour or more without loss of more than 50% of the molecule.

Examples of FDCA precursors include, but are not limited to, 2-hydroxymethyl-5-furan carboxylic acid (HFCA), 2-formyl-5-furan carboxylic acid (FFCA), and FFCA-diketal free acid, and ester derivatives of any of them including, but not limited to, a $C_{1-8}$ straight or branched chain alkyl ester and other esters described herein. In many laboratory conditions the FFCA-diketal molecule (free acid or ester) can exist in equilibrium with FFCA and can therefore be considered an FDCA precursor. Under certain conditions (as also shown herein) the FFCA-diketal can be isolated from an organic solvent in pure form. The diketal is quickly hydrolyzed to the aldehyde, thus producing FFCA upon mixing with water and acid. The esters can be carboxylic acid esters. The ester can be any alkyl ester and examples include, but are not limited to, methyl esters, ethyl esters, propyl esters, isopropyl esters, butyl esters, isobutyl esters, sec-butyl esters, and tert-butyl esters. But any alkyl group can be used to form an ester in the invention. Any of the free acid or any of the esters can be utilized in the reactions of the invention.

An example of conditions for the oxidation of the FDCA precursors include, but are not limited to, performing the oxidation in organic alcohols or in mixtures of organic alcohols with other organic solvents (such as acetone, acetonitrile, DMSO, acetic acid) or in the presence of small amounts of water (e.g. 15% v/v or less). When in aqueous solvent the oxidation reactions can be performed at a pH of 1-3, but in other embodiments the pH can be less than 5.0 or less than 4.0 or less than 3.0 or less than 2.0 or at a pH of 1-3 or 1-4 or 1-5 in aqueous solvents or, when in organic solvents in the presence of a mineral or organic acid. The oxidation reaction can be done in the same reaction and solvent as the dehydration reaction through the addition of an oxidant (e.g. $O_2$ or $H_2O_2$, with or without the presence of catalyst).

Dehydration and Catalysts

For the dehydration reaction or step on 5KGA, 2KGA and DHG (or their esters) a number of chemical dehydration catalysts and conditions can be used, including acid or base catalysts. Mineral acids (e.g., $H_2SO_4$, HCl, HBr, $H_3PO_4$, $HNO_2$, $H_3BO_3$) or immobilized acids (e.g., DOWEX® 50×8, AMBERLYST® or similar ion exchange resins,) and their combinations can be used. Other dehydration catalysts such as clays and microporous, aluminosilicate minerals (e.g., zeolites) can also be used as dehydration catalysts, which also can be immobilized. In other embodiments any solid support or derivatized silica can be used. These reactions can be performed in aqueous, organic, or mixed aqueous organic solutions, as described herein. Mineral acids are acids derived from one or more inorganic compounds and form hydrogen ions and the conjugate base ions when dissolved in water.

For the dehydration in organic solvents 5KGA, 2KGA and DHG (or any of their esters as described herein) can be used. The ester can be synthesized in a separate step or in situ prior to the dehydration, as convenient. A method for the continuous dehydration of fructose to HMF has been recently described for (G-Y Jeong, et al *NPG Asia Materials*, 2015, 7, e173). Conditions under which fructose is dehydrated to HMF can also be useful for the dehydration of the gluconic acid derivative to the FDCA precursor.

When an acid catalyst is used as the catalyst for the dehydration reaction of the present invention it can be any suitable acid. Examples of acid catalysts that can be useful in the invention include, but are not limited to, $H_3PO_4$, $H_2SO_4$, HCl, $HClO_4$, HBr, $Nb_2O_3$ (niobium oxide), polystyrene sulfonic acid, mineral acids (including, but not limited to, the aforementioned), an immobilized acid comprising a sulfonic group in a polymeric backbone or in a copolymer, silica, or ethyl benzene on polystyrene. The acid catalyst can also be an immobilized acid comprising a copolymer, (e.g., a copolymer of polystyrene and divinylbenzene, sulfonated or unsulfonated (e.g. AMBERLITE™) or ethylvinyl benzene, or polymers of acrylates such as, for example, methylacrylate, methylmethacrylate (MMA), butylmethyl acrylate (BMA). They can also include silica derivatized with propylsulfonic acid. In addition to the above, organic acids can also be used as catalysts, such as p-toluenesulfonic acid, acetic acid, formic acid, propionic acid, butyric acid, valeric acid, caproic acid, oxalic acid, lactic acid, malic acid, citric acid, benzoic acid, and carbonic acid. The acid catalysts named are only examples and, in addition to the above, any Lewis acid can be utilized (e.g., one that leads to a more reactive electrophile). Catalysts that are basic can also be used in the dehydration reaction of the invention. Examples of base catalysts include, but are not limited to, $Na_2CO_3$, NaOH, and KOH, or immobilized bases (e.g. DOWEX® 1×8, AMBERLITE™ and others). These catalysts can be used under the same solvents and conditions as the ones described earlier for acids. AMBERLYST® and DOWEX® are (anion or cation) ion exchange resins known in the art that have a rigid macroporous structure similar to conventional adsorbents that is superimposed on the gel structure. They can be generally referred to as macroreticular ion exchangers. In some embodiments they can be sulfonic acid type based upon a polystyrene or styrene-divinylbenzene (DVB) copolymer and a particle size of less than 300 um. In various embodiments the surface area of square meters per gram of resin can be greater than 1 or greater than 2 or greater than 5 or greater than 10 or greater than 15 or greater than 20 or greater than 25 or greater than 30 or greater than 35 or greater than 40 square meters per gram of resin. AMBERLYST® can function as a solid acid or base catalyst, or as a recyclable catalyst. In one embodiment the AMBERLYST® is AMBERLYST® 15 in the hydrogen form. In various embodiments any of the ion exchange resins described herein can be utilized in the invention with 4% divinyl benzene (DVB) or 8% DVB or 10% DVB or 16% DVB.

In some embodiments the FDCA precursor molecules formed according to the invention can then be further converted into FDCA. This can be done through oxidation of the FDCA precursor to form FDCA. Many conditions for the chemical oxidation of alcohols and aldehydes to form carboxylic acids are known in the chemical literature and these conditions can also be used in the present invention for the oxidation of FDCA precursors to FDCA. In some embodiments the HFCA or FFCA can be oxidized into FDCA under acidic conditions. A number of examples for the aerobic oxidation of HMF using catalysts have been reported (e.g., Saha, B et al., *Catal. Sci. Technol.*, 2012, 2, 79-81; Liu, B et al., *Green Chem.*, 2015, 17, 1610-1617). In various embodiments the oxidation conditions can involve the use of homogenous $Co(OAc)_2/Zn(OAc)_2/Br^-$ and heterogeneous $Au-TiO_2$ and $Au-CeO_2$ catalysts, which can be nanoparticulate catalysts. Additional catalysts include immobilized Pt or Pd, for example immobilized in carbon or $Al_2O_3$. It can also utilize a Pd catalyst, which can be a $Pd/CeFe_3O_4$, Pt/C, Pd/C, Pt—Ru/C, or any one or more of the catalysts listed in Table 2. Any of the catalysts can be nanoparticle catalysts. The conversion can be done with or without a trifluoroacetic acid additive, and can be done under aerobic conditions. $H_2O_2$ or oxygen can also be included for the oxidation with any of the catalysts named herein. The conversion can also be done using air or oxygen as a co-reactant in medium to high temperature pressure which, in various embodiments can be 50-250° C. or 100-200° C. or 50-300° C. or 50-350° C. The pressure can be 10-500 psi or 10-200 psi or 10-300 psi or 100-350 psi or 100-500 psi or 1-100 psi or 1-200 psi or 1-500 psi or 1-1000 psi.

In some embodiments the FDCA precursor can be oxidized into FDCA under the same conditions used and in the same solvent or reaction media used as the dehydration reaction for the formation of the FDCA precursor from the gluconic acid derivative (e.g., the DHG, 5KGA, or 2KGA). In some embodiments the method is performed without a step of purifying the HFCA or FFCA. Oxidation of FFCA to FDCA may be easily achieved at the same time as the dehydration by performing the reaction under aerobic (or bubbling air or oxygen conditions) with or without the use of an oxidation catalyst. In other embodiments the FDCA precursor can be oxidized in a separate reaction.

Other chemical catalysts include, but are not limited to resins based on crosslinked polystyrene. Any of the ion exchange resins can have functional groups selected from any one or more of the following types: strongly acidic resins that can have sulfonic acid groups (e.g. sodium polystyrene sulfonate or polyAMPS); strongly basic resins having quaternary amino groups (e.g. trimethylammonium groups, e.g. polyAPTAC); weakly acidic resins having carboxylic acid groups; and weakly basic resins having primary, secondary, and/or tertiary amino groups, e.g. polyethylene amine. Any of the types of resins and any of the groups can be used alone or in combination with other resin types and/or groups on the resins, as desired.

The useful concentration of any of the dehydration catalysts described herein for the dehydration reactions is easily determined for the specific reaction, but in various embodiments the concentration of dehydration catalyst is 25 mM-1 M or 50 mM to 1 M or 100 mM to 1 M or 1-5 M or 1-6 M or 1-7 M or 1-10 M.

Solvents

The dehydration reaction of the invention can be performed in a wide variety of solvents. In various embodiments the reaction can be performed in a solvent that is an aqueous, organic, or mixed aqueous/organic solution. In various embodiments the solvent can be anywhere from 1% to about 99% aqueous solution or liquid. The aqueous solution can be water. In other embodiments the solvent can be at least 5% aqueous solution, or at least 10% aqueous solution or at least 20% aqueous solution or at least 30% aqueous solution or at least 40% aqueous solution or at least 50% aqueous solution or at least 60% aqueous solution or at least 70% aqueous solution or at least 80% aqueous solution or at least 90% aqueous solution or about 100% aqueous solution, with the remaining portion being an organic, miscible, or immiscible solvent. The solvent can be a mixed solvent containing aqueous solution and a miscible or immiscible solvent, such as those described herein. The solvent can also be an organic solvent either mixed with water or 100% organic solvent. When the solvent is an organic solvent, whether all organic solvent or mixed with an aqueous solution in the amounts described herein, it can be acetone, acetic acid, DMSO, acetonitrile, an alkyl alcohol, such as methanol, ethanol, propanol, isopropanol, butanol, isobutanol, sec-butanol, tert-butanol, pentanol, hexanol, septanol, or oxanol, or any alkyl alcohol, or a $C_{1-3}$ or $C_{1-4}$ alcohol. Ethers can also be used as a solvent for the reaction including, but not limited to, tetrahydrofuran, methyl tetrahydrofuran, diethyl-ether, diisopropyl ether, methyl-tert-butyl ether, and 1,4-dioxane. In addition, other common solvents can also be used including, but not limited to, dimethysulfoxide, acetone, acetic acid, acetonitrile, and an aqueous mixture of any of these. Any of the solvents that are mixtures of organic solvent and aqueous solution can have the percentages of water described herein.

The reactions described herein can be performed in any of a variety of methods and the following presents only one possible method for illustration. All references to DHG, 5KGA, 2KGA, FFCA, FFCA-diketal, HFCA, and to any gluconic acid derivative or FDCA precursor, include a reference not only to their free acids, but also to any of their esters, as described herein. The Figures describe steps of the invention, which are described in further detail herein.

Step 1. Step 1 of a reaction path useful in the invention can be the conversion of glucose into gluconate or gluconic acid (FIG. 1). This reaction can be performed by the conversion (oxidation or dehydrogenation) of glucose to 1,5-gluconolactone, followed by the conversion (e.g., hydrolysis) of 1,5-gluconolactone to gluconate.

The conversion of glucose into 1,5-gluconolactone can be performed with various enzymes, such as those of the family oxygen dependent glucose oxidases (EC 1.1.3.4) or NAD (P)-dependent glucose dehydrogenases (EC 1.1.1.118, EC 1.1.1.119). In some embodiments enzymes of the family of soluble and membrane-bound PQQ-dependent enzymes (EC 1.1.99.35 and EC 1.5.2) found in *Gluconobacter* and other oxidative bacteria can also be used. *Gluconobacter oxydans* contains dehydrogenases from both families that can efficiently oxidize glucose to gluconic acid when grown in a fermenter. Glucose dehydrogenases containing FAD cofactor and that belong to the EC 1.1.5.9 enzyme family can also be used. The specific enzyme selected will be dependent on the desired reaction conditions and necessary co-factors that will be present in the reaction. Conditions for glucose oxidases are well known, and the enzyme functions in a wide variety of conditions, for example pH 5-6 or 4-7 or 3.5-7.5. Similarly the conditions for the glucose dehydrogenases are broad and well known, for example pH 3.0-5.5, 6-7.5 or 6-8 or 6-9.0 or 6-9.5.

The conversion (e.g., hydrolysis) of 1,5-gluconolactone to gluconate can be performed chemically in aqueous media and the rate of hydrolysis is dependent on pH (Shimahara, K, Takahashi, T., *Biochim. Biophys. Acta* (1970), 201, 410). Hydrolysis may be faster in basic pH and slower in acid pH (e.g. pH 7.5 or 7-8 or 6-9 or 6.5-8.5). Many microorganisms also contain specific 1,5-glucono lactone hydrolases, and a few of them have been cloned and characterized (EC 3.1.1.17; Shinagawa, E., *Biosci. Biotechnol. Biochem.* 2009, 73, 241-244).

Step 2. Step 2 involves the conversion of gluconate to 5KGA. A number of enzymes of the family of NAD(P)-dependent dehydrogenases (EC1.1.1.69) have been cloned and shown to have activity for the oxidation of gluconate or the reduction of 5KGA. For example, the NADPH-dependent gluconate 5-dehydrogenase from *Gluconobacter* (Expasy P50199) was synthesized for optimal expression in *E. coli* and has been cloned in pET24 (pSGI-383). The enzyme was expressed and shown to have the required activities. Additional enzymes useful for performing this step include those of the family of PQQ-dependent enzymes present in *Gluconobacter* (Peters, B. et al. *Appl. Microbial Biotechnol.*, (2013), 97, 6397). Enzymes from these families can also be used to synthesize 5KGA from gluconate. Step 2 also involves the oxidation of gluconic acid to 2KGA. Similar to 5KGA many different enzymes can catalyze this reaction, including soluble cytosolic NAD(P)-dependent (EC 1.1.1.215) and membrane-bound FAD-dependent enzymes (EC 1.1.99.3). *Gluconobacter oxydans* has been shown to efficiently oxidize glucose to gluconic acid and 5-ketogluconate (5-KGA) when grown in a fermenter (G. Keliang, W. Dongzhi Appl. Microbiol. Biotechnol. 2006, 70, 135). *Gluconobacter oxydans* can also efficiently produce 2KGA when grown in a fermenter. Other engineered or wild type bacteria or yeasts can be used for the production of 2KGA or 5KGA through fed batch or continuous fermentations from glucose or other hexoses or mixtures. Engineered acetic acid bacteria that produce high titers (of greater than 150 g/L of either 5KGA or 2KGA) have been engineered.

Step 3. Step 3 involves the conversion of gluconate to DHG. Several enzymes, such as gluconate dehydratases, can be used in the dehydration of gluconic acid to dehydro gluconic acid (DHG). Examples include those belonging to the gluconate dehydratase family (EC 4.2.1.39). A specific example of such a dehydratase has been shown to dehydrate gluconate (Kim, S. Lee, S. B., *Biotechnol. Bioprocess Eng.* (2008), 13, 436).

Steps 4 and 5. Step 4 involves the conversion of 5KGA into the FDCA precursor FFCA, as described herein. Step 5 involves the conversion of 2KGA into FDCA precursor FFCA. Steps 4 and 5 can involve passing through a transient intermediate before conversion to FFCA, as shown in FIG. 2 for intermediates A and B. These reactions are performed according to the invention, as described herein.

Step 6 is the conversion of FFCA to FDCA. This can be performed via an oxidation reaction, which can be performed immediately after the production of FFCA in the same solvent or mixture, as described herein. This can also be performed in a separate reaction after FFCA has been isolated. Various conditions for the chemical oxidation of alcohols and aldehydes to form carboxylic acids are known in the chemical literature and can be used for the oxidation of FFCA and HFCA. A number of examples for the aerobic oxidation of HMF using catalysts have been reported (i.e: Saha, B et al., Catal. Sci. Technol., 2012, 2, 79-81; Liu, B et al., *Green Chem.*, 2015, 17, 1610-1617). These conditions are also useful for the oxidation of FFCA. Oxidation of FFCA to FDCA can be achieved at the same time as the dehydration step by performing the reaction under aerobic conditions (or bubbling air or oxygen conditions), either with or without the use of an oxidation catalyst. In another embodiment the oxidation can be performed in the same media as the dehydration reaction, after the dehydration has been completed. In another embodiment enzymes capable of oxidizing FFCA to FDCA can be used (e.g., Dijkman W P, et al., *Angew. Chem. Int Ed*, 2014, 53(25), 6515).

Step 7 is the conversion of DHG into HFCA. This reaction can involve passing through an intermediate, as depicted in FIG. 3. The reaction is performed as described herein. Step 8 is the conversion of HFCA into FDCA via an oxidation reaction, as described herein.

As seen from this disclosure and the Examples provided below, the conditions of the reactions of the invention can be very broad and varied while still obtaining a desirable result according to the invention. The person of ordinary skill in the art with resort to this disclosure will be able to manipulate the reaction conditions to obtain a desirable result for the specific goals and conditions involved.

In some exemplary embodiments the synthesis of the FDCA precursor can begin with DHG or 2KGA or 5KGA, or with a methyl, ethyl, propyl, $C_{1-4}$ or $C_{1-6}$ alkyl, alcohol, or carboxylic acid derivative of any of them, which can be provided at a concentration of at least 25 mM, or 50 mM to 500 mM, or 50 mM to 1 M, or 1-2 M, or 1-5 M or 1-6 M or 1-7 M or 1-10 M. The dehydration catalyst can be an acid catalyst such as $H_2SO_4$, HCl, $HClO_4$, HBr, $Nb_2O_3$, or $H_3PO_4$, or an immobilized acid such as an AMBERLYST® or DOWEX® as described herein, or a copolymer of polystyrene and divinylbenzene, or zeolite. A mineral acid can be provided at a concentration of 25 mM-1 M or 100 mM to 1 M or 1-6 M. In various embodiments the reaction solvent can be 100% water or acetic acid in water (e.g. at least 50% acetic acid or at least 60% acetic acid or at least 70% acetic acid, all in water).

In a batch reaction or under flow conditions the reaction can be performed at a temperature of 30-100° C. or 30-150° C. or 30-200° C. or 50-150° C. or 70-130° C. or 70-100° C. or 70-90° C., and the solvent can be water or an aqueous solvent. The reaction can be allowed to proceed for at least 15 minutes or at least 30 minutes or 15 minutes to 2 hours or at least 2 hours or at least 4 hours or at least 8 hours or at least 12 hours or at least 15 hours, or from 15 minutes to 24 hours or from 15 minutes to 48 hours. Under batch or flow conditions the reaction can be optionally performed under pressure such as at 10 psi to 100 psi or at least 10 psi or at least 20 psi or about 30 psi or 10-50 psi or at greater than 50 psi.

In a specific embodiment the methods involve a chemical dehydration reaction utilizing DHG, 2KGA, or 5KGA as substrate at 50 mM to 1M or 1-2 M in a batch reaction with a soluble acid catalyst, such as $H_2SO_4$, HBr, HCl at 1-5M or immobilized acids in polymer supports such as DOWEX®, or AMBERLYST® at a temperature of 50-100° C. or 100-150° C. The solvent can be water, acetic acid, methanol, ethanol, acetone, dimethylsulfoxide, tetrahydrofuran or a mixture of any of the organic solvents with water. Water mixed with non-miscible organic solvent such as ethers (diethyl, methyl-isopropyl etc), esters (ethyl-acetate etc), alcohols (tert-butanol, butanol, propanol etc). The reactions can be performed under atmosphere or in oxygen free inert gases such as nitrogen or argon. The reaction can take place for 10-60 min or 1-4 h or 6-12 h or at least 10 minutes or at least 1 hour. Catalytic amounts of zeolites or Lewis acids (such as for example $Al_2O_3$, $TiO_2$) can be added in any of the previous reactions. In another embodiment the method utilizes a Dean Stark apparatus, the substrate is DHG, 2KGA, or 5KGA, the solvent is butanol, the catalyst is $H_2SO_4$ or any of the acids described herein. The reaction can occur at 20-60° C. or 30-50° C. for 20-60 hours or 30-50 hours before being transferred into a Dean Stark apparatus. After transfer the reaction can be heated to 100-180° C. or 120-160° C. for 2-6 hours or 3-5 hours.

In another specific embodiment the method can be a continuous flow method with DHG, 2KGA, or 5KGA as substrate, the solvent can be water, ethanol, methanol, a water/methanol mixture, or acetic acid in water, and the temperature can be 70-100° C. or or 70-130° C. or 70-170° C. or 70-150° C. The acid catalyst can be $H_2SO_4$, HCl, $HClO_4$, HBr, $Nb_2O_3$, or $H_3PO_4$, or an immobilized acid such as an AMBERLYST® or DOWEX®, which can be present at 1-5M. The previous mineral acid catalysts can be mixed with the 5KGA, 2KGA or DHG just before entering the heated flow reactor (at any of the previous temperatures) or mixed in a stock solution kept at 4-10° C. or 10-30° C. prior to entering the column. The flow reactor can contain an immobilized acid such as DOWEX®, AMBERLYST® or derivatized silica or zeolite or an inert material such as sand. The reaction time in the flow reactor can vary from a 1-10 min or 10-20 min or 20-60 min. The reactions (batch or flow) can be performed in the presence of atmospheric oxygen or under oxygen-free conditions such under nitrogen or argon atmosphere.

In another embodiment the method utilizes a Dean Stark apparatus, the substrate is DHG, 2KGA, or 5KGA, the solvent is butanol, the catalyst is $H_2SO_4$ or any of the acids described herein. The reaction can occur at 20-60° C. or 30-50° C. for 20-60 hours or 30-50 hours before being transferred into a Dean Stark apparatus. After transfer the reaction can be heated to 100-180° C. or 120-160° C. for 2-6 hours or 3-5 hours.

In another aspect the invention provides methods for the synthesis of an FDCA precursor involving oxidizing glucose into gluconic acid, enzymatically oxidizing the gluconic acid into keto-gluconic acid (or di-ketogluconic acid), performing a dehydration reaction to convert the keto-gluconic acid (or di-keto-gluconic acid) into an FDCA precursor. In one embodiment the FDCA precursor is FFCA.

In another aspect the invention provides a method for the synthesis of an FDCA precursor. The method can involve oxidizing glucose into gluconic acid, enzymatically dehydrating the gluconic acid into dehydro-gluconic acid (DHG), and performing a dehydration reaction to convert the DHG into an FDCA precursor. In one embodiment the FDCA precursor is HFCA.

The following Examples provide further, non-limiting examples of the methods of the invention.

EXAMPLE 1

Dehydration of DHG in Aqueous Media in Batch Reactions

In each of three vials containing 4 ml of water 50 mg of DHG (70 mM) was dissolved. The following acids were then added: 1) 0.5 ml of concentrated $H_2SO_4$; 2) 130 mg DOWEX® 50×8 (H form) or 3) 130 mg AMBERLYST® 15 (H form). All reactions were incubated at 75° C. with good stirring. Reaction progress was analyzed by both TLC and HPLC using commercial 2-hydroxymethl-5-furan (HFCA) carboxylic acid as an authentic standard. Synthesis of HFCA was observed in all reactions reaching a yield of 5-10% after overnight reaction. The HFCA produced from these reactions was analyzed by MS spectra and was found to have the same retention time as the authentic standard. These results show that HFCA was produced from DHG when the DHG was subjected to a dehydration reaction through an acid catalyst.

In a separate experiment, 5 mL of an ethanol/water mixture (v/v, 9/1) containing 1.5 M of $H_2SO_4$ and 200 mM of purified DHG was placed in two vials. One vial was incubated with stirring at 80° C. and the other at 100° C. for 18 hours. HPLC analysis of the reactions confirmed the formation of HFCA at about 70% molar yield for the 80° C. reaction and about 55% yield for the reaction at 100° C. (and >95% conversion). The previous yield includes both HFCA free acid and the HFCA-ethyl ester (about 1/1 ratio in each reaction). The product identity and quantification was done by comparison with authentic standards by HPLC.

EXAMPLE 2

Dehydration of DHG and 2KGA in Flow Reactors

In this example reactions were performed under flow conditions using a flow reactor system (i.e. as continuous flow reactions). A stock solution of DHG was prepared by dissolving DHG in AcOH/$H_2O$ (v/v, 80/20) containing 1.5 M of HBr, to a final concentration of 200 mM. This solution was kept at ambient temperature (about 20° C.) and was passed through the reactor that was heated at either 100° C. or 120° C., at a pressure of 30 psi to keep solvents from evaporating. The reactor consisted of a glass column packed with 3 mL of sand. The flow rate was 0.05 mL/min, thus allowing a residence time in the column of about 40 min. Analysis of various samples at each temperature revealed that the reaction at 120° C. gave 50-70% yield of HFCA while the reaction at 100° C. produced 25-30% yield to product in addition to unreacted DHG (15%).

The same experiment was also performed using 2KGA as substrate, except that the reactor temperature that was kept at 80° C. or 120° C. With 2KGA, higher yields (about 50%) to FFCA were obtained at lower temperature, however, an additional unidentified product (possibly furfuraldehyde) was also detected. When the reaction was performed at 120° C., the yield to FFCA was reduced (about 15%) and two additional aromatic products were detected.

EXAMPLE 3

Dehydration of 2KGA and 5KGA in Aqueous Media in Batch Reactions

A number of different reactions were prepared according to Table 1 with 2KGA (200 mM) and 5KGA (200 mM) according to the conditions indicated. The reactions were incubated at 120° C. for 30 min before a sample was taken and analyzed by HPLC/MS. The formation of FFCA was confirmed and quantified by comparison with authentic material, and the amount produced, along with the conversion to products, is shown in Table 1.

FDCA precursor aldehyde can be oxidized immediately to FDCA under the dehydration conditions if done in the presence of an oxidant, for example, bubbling oxygen, hydrogen peroxide or other oxidizing agents and catalysts.

The percent of FDCA precursor produced can be from about 0.2% to about 1%, or from 0.2% to about 1.5% or from 0.2% to about 2%, or 0.2%-5%, or 0.2%-7%, or about 1%, or about 1.5%, or from about 0.5% to about 7%, or from about 0.5% to about 10%, or from about 0.1% to about 5%, or from about 0.1% to about 7%, or from about 1% to about 10%, or more than 0.1%, or more than 0.2%, or more than 0.5%, or more than 1.5%, or about 2%, or more than 2%, or more than 5% or more than 7%, or more than 10%, or more than 25%, or more than 50%, or more than 60%, or more than 70%, or more than 80%, all w/w. But optimization of conditions will result in much higher yields.

EXAMPLE 4

Dehydration of 5KGA in a Dean Stark Apparatus

In 30 mL of BuOH in a round flask 2 gm of potassium 5-ketogluconate was added, along with 0.2 mL of concentrated sulfuric acid and 100 mg of chloride derivitized silica (esterification catalyst). The reaction was stirred at 40° C. for 40 h before it was transferred in a Dean Stark apparatus. An additional 0.3 mL of $H_2SO_4$ was then added to the mixture and the reaction was heated at 140° C. for 4 hours under nitrogen atmosphere. The extent of 5KGA esterification prior to the dehydration was not measured.

Figure 4:
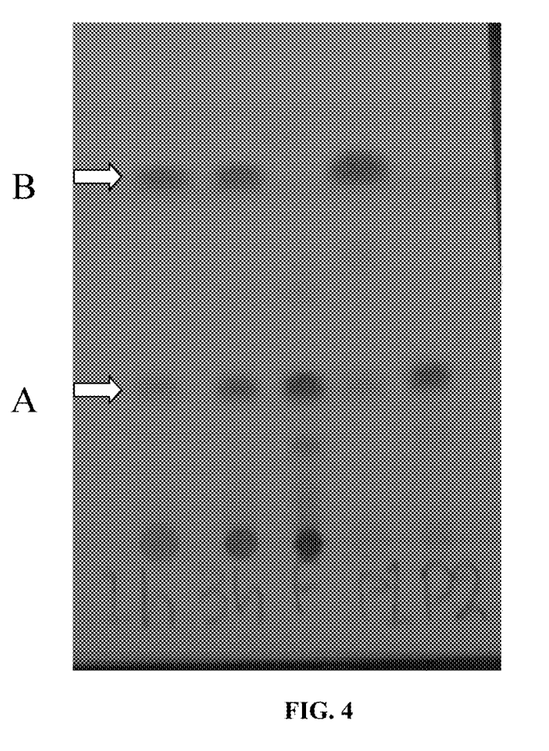

TLC analysis showed the formation of two products with UV absorbance at 1 hour and 3 hours (FIG. 4). The reaction was terminated at 4 h because prior experience indicated that this was usually the time for a complete reaction under these conditions. Analysis by 1H NMR showed the formation of two major compounds and no 5KGA remaining, and therefore it was thought the dehydration was complete. At this point the mixture was cooled to room temperature, and was mixed with 100 mL of methyl-tetrahydrofuran. The combined organic solution was extracted once with 50 mL water and 50 mL saturated sodium chloride. The organic layer was evaporated to dryness giving 2.2 gr of a dark viscous liquid.

TABLE 1

| Solvent | Acid (mL added) | [Acid] | 2KGA % Conversion | 2KGA % FFCA | 5KGA % Conversion | 5KGA % FFCA |
|---|---|---|---|---|---|---|
| AcOH (3.5 mL) $H_2O$ (0.5 mL) | $H_2SO_4$ (0.3 mL) | 1M | 98 | 3.5 | 99 | 1.1 |
| AcOH (3 mL) $H_2O$ (0.5 mL) | $H_2SO_4$ (1.4 mL) | 5M | 100 | 6.7 | 100 | 0.0 |
| AcOH (3.5 mL)/$H_2O$ (0.5 mL) | AMBERLYST ® (50 mg) | | 91 | 0.3 | 93 | 1.0 |
| AcOH (3.5 mL)/$H_2O$ (0.5 mL) | DOWEX ® 50x8-H+ (50 mg) | | 89 | 0.3 | 98 | 0.0 |
| AcOH (3.2 mL) $H_2O$ (0.3 mL) | Perchloric acid (0.8 mL) | 2M | 99 | 3.8 | 99 | 0.5 |
| AcOH (4 mL) | HBr (1.1 mL) | 2M | 100 | 0.6 | 100 | 0.2 |
| AcOH (4.0 mL) $H_2O$ (0.2 mL) | HCl (0.8 mL), NaBr (100 mg) | 2M, 0.2M | 100 | 3.0 | 100 | 1.5 |
| AcOH (4.0 mL) $H_2O$ (0.3 mL) | $H_3PO_4$ (0.7 mL), $Nb_2O_3$ (67 mg) | 2M, 50 mM | 95 | 2.6 | 94 | 0.0 |
| $H_2O$ (3.5 mL) | $H_2SO_4$ (1.4 mL) | 5M | 100 | 7.1 | 100 | 0.0 |
| $H_2O$ (3.5 mL) | HBr (1.1 mL) | 2M | 99 | 5.2 | 99 | 0.9 |

Figure 5A:
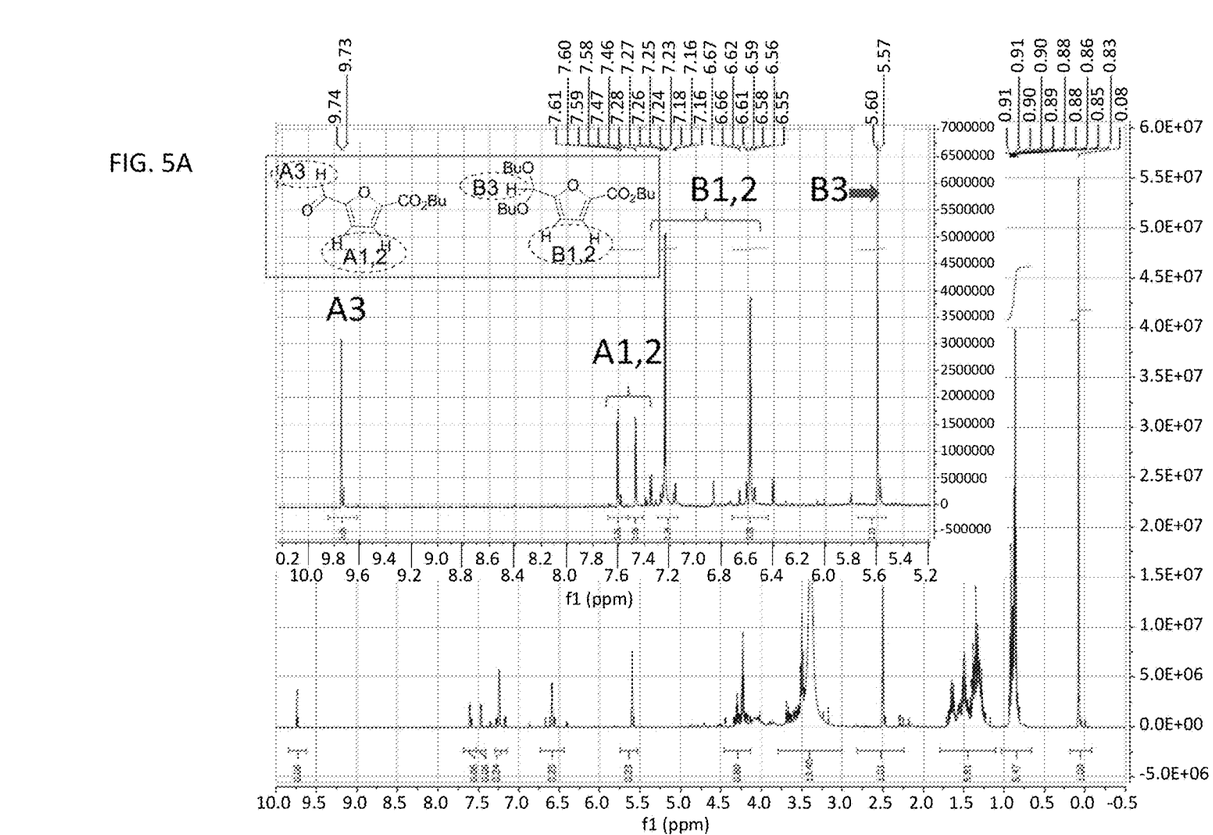
FIG. 5A shows an NMR spectra of crude reaction mixture in a Dean Stark apparatus before purification.
Figure 5B:
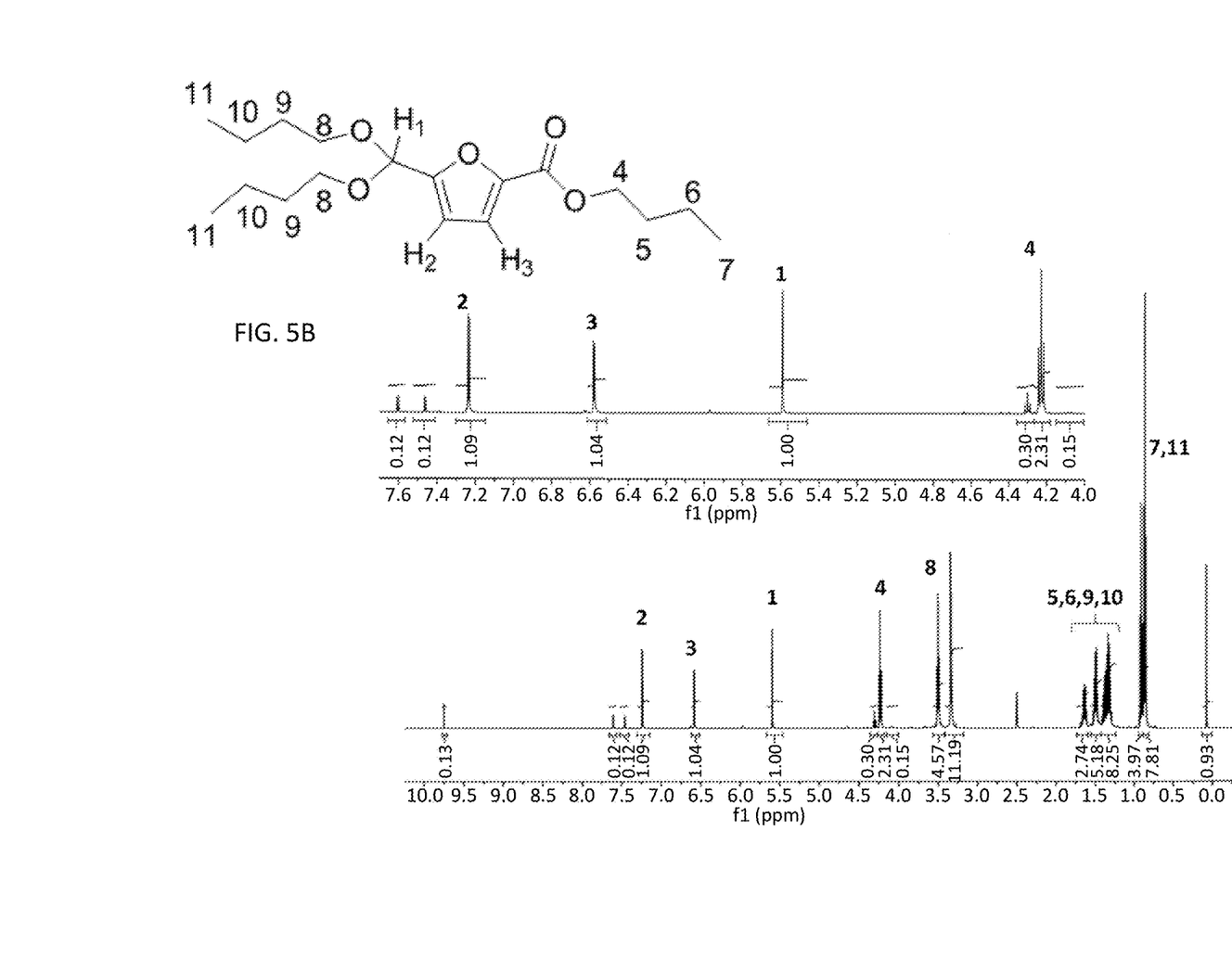
FIG. 5B shows an NMR spectra of purified compound B (also P2 from lane 4 of FIG. 4).
Figure 5C:
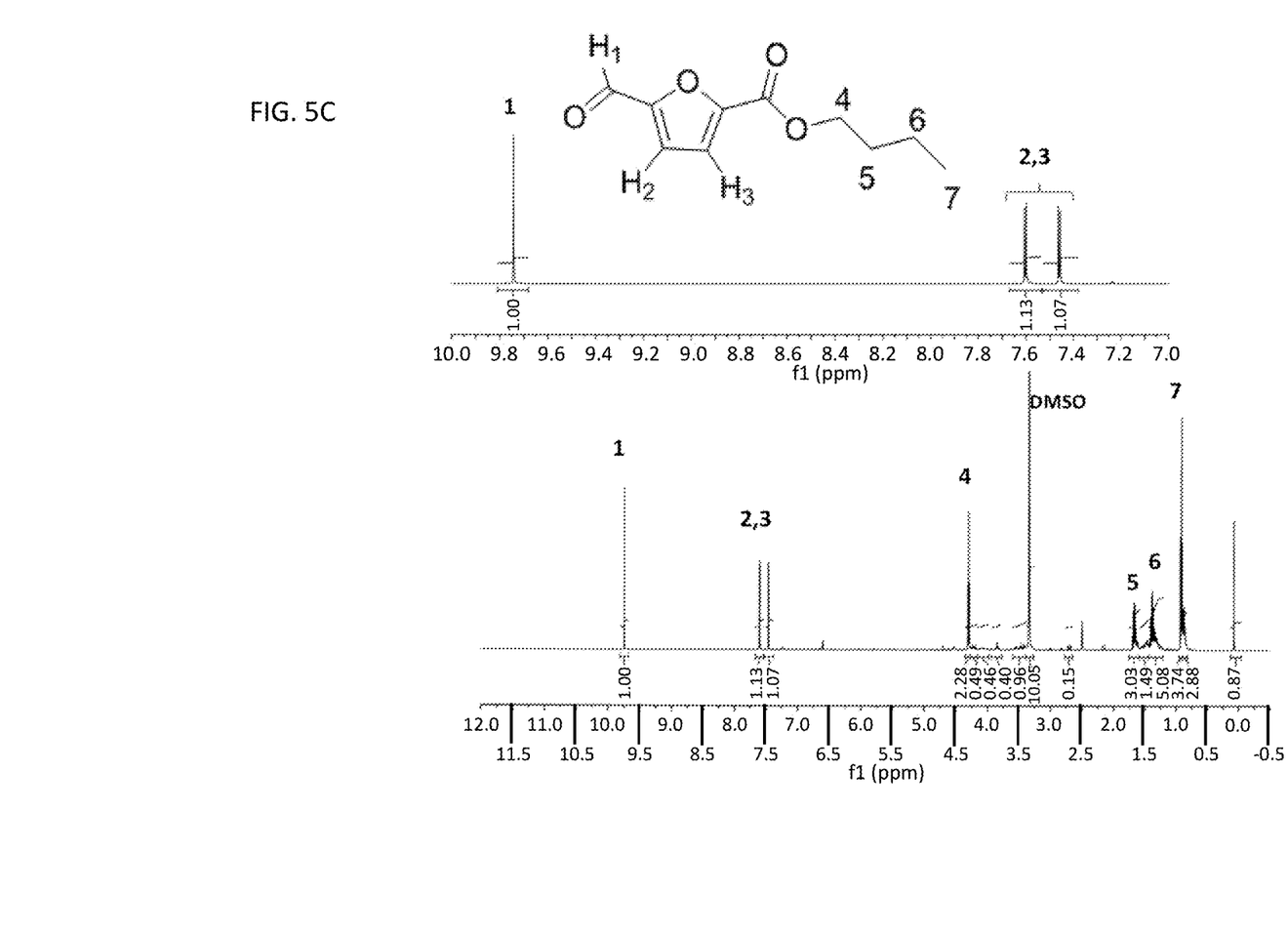
FIG. 5C provides an NMR spectra of compound A (lane 5 of FIG. 4)
Figure 5D:
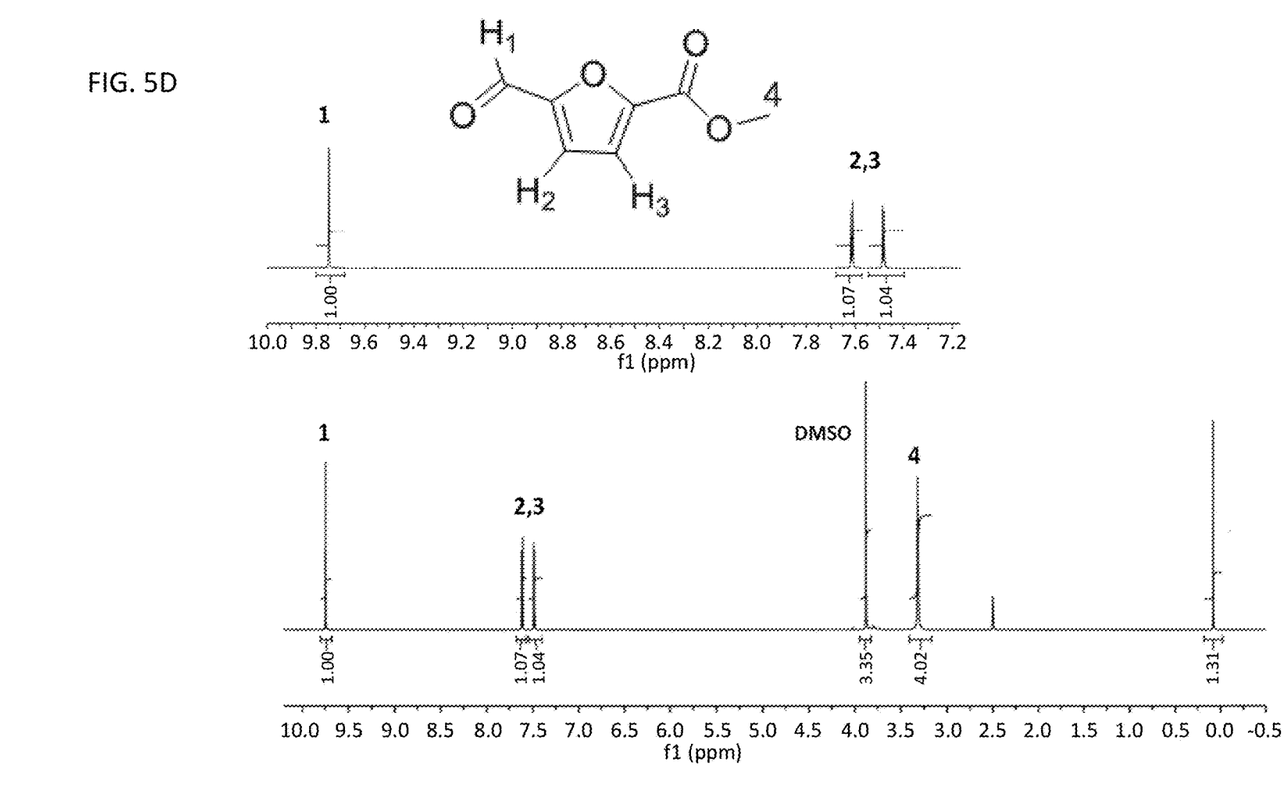
FIG. 5D shows an NMR spectra of authentic methyl-2-formyl-5-carboxyfuran.

Both compounds reacted very quickly as illustrated by the high conversions shown in Table 1. Furthermore even without optimization of conditions both reactions produced FFCA (1-7% yield). Even higher yields will be available by optimizing the conditions as described herein. The produced Two compounds, A and B, were visible by TLC and were purified using flash chromatography with a silica column and TLC running buffer (buffer 85/15 v/v hexane/ethylacetate) to yield about 150 mg as a viscous oil of each. Analyses of the purified compounds are shown in lanes P1 and P2 of FIG. 4. The purified compounds along with the crude reaction mixture (at the end of the reaction after work-up) were analyzed by 1H NMR as shown in FIGS. 5a through 5c, with FIG. 5d showing an NMR spectra of authentic methyl-2-formyl-5-carboxyfuran for comparison. The MS of the two purified compounds was also measured.

Figure 6:
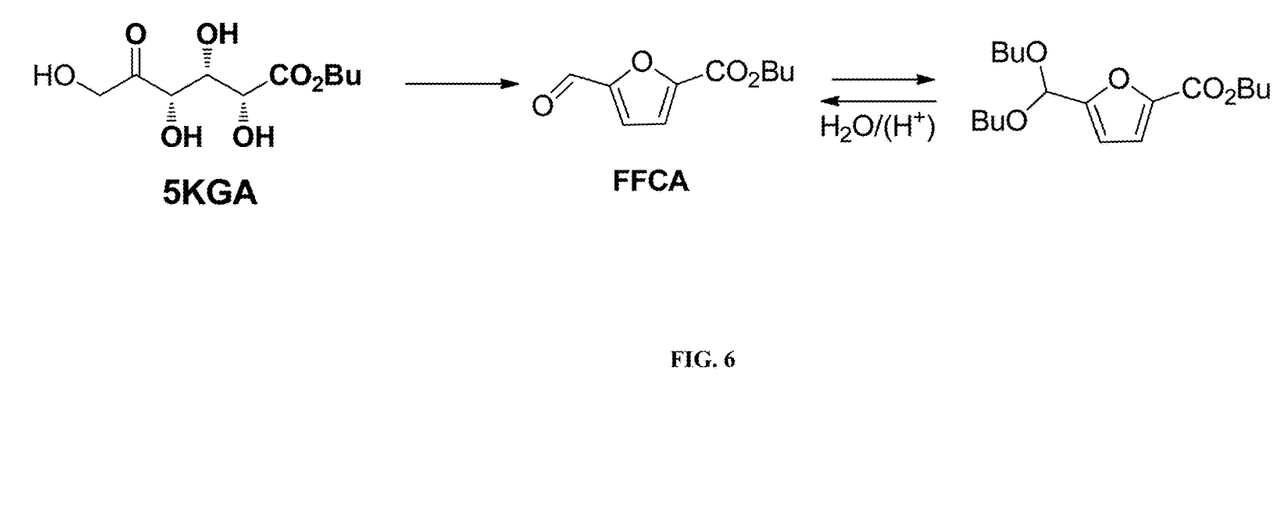
FIG. 6 shows a reaction illustrating the dehydration products of 5KGA in butanol with acid.

All these data, including the TLC and NMR data, confirm that the dehydration of butyl-5KGA forms two major products, the butyl aldehyde A (FIG. 5a) and the FFCA hemiketal B (FIG. 5a), which upon incubation with acid water quickly hydrolyzes to the aldehyde A. Therefore, the dehydration of 5KGA in butanol follows the reaction path shown in FIG. 6.

A total amount of 0.3-0.4 gr of combined compounds A and B was isolated after purification. This corresponds to a yield of 15-20% from 5KGA. Optimization of this reaction can be achieved (including in situ oxidation as described herein) to increase the yield even further.

Dehydration of fermentation or enzymatically produced DHG, 5KGA or 2KGA may be performed in the aqueous media they were produced without prior purification. In a different aspect of the invention, the compounds may first be isolated as solid powders (by precipitation or other method).

EXAMPLE 5

Oxidation of HFCA to FDCA

This examples shows the oxidation of the FDCA precursor (here FFCA) into FDCA. A series of reactions were prepared as shown in the following Table. All reactions contained 100 mM of commercial FFCA. The reactions were performed in screw capped vials under air (in all reactions with $H_2O_2$ and controls runs #11-13) or under oxygen at about 20 psi. All reactions were incubated for 20 h before samples were analyzed by TLC for product formation.

TABLE 2

| RXN | Solvent | Catalyst | Oxidant | Temp | Conversion[1] |
|---|---|---|---|---|---|
| 1 | AcOH(4.5 mL)/THF(2.5 mL) | CoNO3/MnNO3 (5 mM each) | O2 pressure | 90° C. | About 25% |
| 2 | AcOH(4.5 mL)/THF(2.5 mL) | CoNO3/MnNO3 (5 mM each) | O2 bubble | 80° C. | About 25% |
| 3 | AcOH(4.5 mL)/THF(2.5 mL) | | H2O2 (0.1 mL 30%) | 80° C. | >90% |
| 4 | H2O, (K2CO3 0.25M) | Pt/C (20 mg) | O2 pressure | 90° C. | ? |
| 5 | H2O, (K2CO3 0.25M) | Pt-Ru/C(20 mg) | O2 pressure | 90° C. | >90% |
| 6 | H2O, (K2CO3 0.25M) | Pd/C (20 mg) | O2 pressure | 90° C. | About 50% |
| 7 | THF (3.5 mL) | | H2O2 (0.1 mL 30%) | 60° C. | About 10% |
| 8 | Methyl-THF (3.5 mL) | | H2O2 (0.1 mL 30%) | 60° C. | About 10% |
| 9 | AcOH (2 mL)/H2O (2 mL) | | H2O2 (1 mL 30%) | 80° C. | >90% |
| 10 | AcOH (4 mL) | | H2O2 (1 mL 30%) | 80° C. | >90% |
| 11 | THF (3.5 mL) | Pt-Ru/C(10 mg) | | 60° C. | trace |
| 12 | Methyl-THF (3.5 mL) | Pt-Ru/C(10 mg) | | 60° C. | trace |
| 13 | AcOH(2 mL)/THF(1 mL) | | | RT | trace |

All reactions conversions described in the Table above are based on TLC analysis. For example, >90% indicates the result of TLC analysis where FDCA was detected as the only product. "About" 50% indicates that FFCA and FDCA spots with similar intensity were observed.

EXAMPLE 6

Enzymatic Synthesis of DHG

In 100 mL buffer containing potassium phosphate (10 mM pH 7.5) and 2 mM of $MgCl_2$, 2.2 g of sodium gluconate was dissolved (100 mM final concentration). After the pH was readjusted to 7.5, 20 mg of lyophilized gluconate dehydratase was added and the reaction was incubated at 35° C. After 8 hours, HPLC-MS analysis revealed complete conversion of gluconate to a single product with a molecular weight corresponding to DHG. Enzymes were precipitated by lowering the pH to 3.5 with the addition HCl, and were removed by centrifugation. The clear DHG-containing solution was lyophilized to produce 2.2 g of a white powder (80-85% w/w DHG salt in this powder). Gluconate dehydratase (EC 4.2.1.39) was expressed from a plasmid in *E. coli* and was purified and lyophilized.

Although the invention has been described with reference to the above examples, it will be understood that modifications and variations are encompassed within the spirit and scope of the invention. Accordingly, the invention is limited only by the following claims.

What is claimed is:

1. A method of synthesizing a 2,5-furan dicarboxylic acid (FDCA) precursor molecule comprising:
   performing a chemical dehydration reaction on 2-dehydro-3-deoxy gluconic acid (DHG) or an ester thereof, 2-ketogluconic acid (2KGA) or an ester thereof, or 5-ketogluconic acid (5KGA) or an ester thereof, in the presence of a dehydration catalyst in a continuous flow reactor;
   thereby synthesizing an FDCA precursor molecule selected from the group consisting of 2-formyl-5-furan carboxylic acid (FFCA) and 2-hydroxymethyl-5-furan carboxylic acid (HFCA).

2. The method of claim 1 wherein the dehydration catalyst is an acid catalyst.

3. The method of claim 2 wherein the acid catalyst is a mineral acid.

4. The method of claim 3 wherein the mineral acid is selected from the group consisting of: $H_2SO_4$, HCl, $HClO_4$, HBr, $Nb_2O_5$, and $H_3PO_4$.

5. The method of claim 1 wherein the dehydration catalyst is an immobilized catalyst.

6. The method of claim 5 wherein the immobilized catalyst comprises a copolymer of polystyrene and divinylbenzene, or zeolite.

7. The method of claim 2 wherein the reaction is performed in a solvent selected from the group consisting of: acetic acid and water, or a mixture of acetic acid and water, or a mixture of an alcohol and water.

8. The method of claim 7 wherein the acid catalyst is selected from the group consisting of: $H_2SO_4$, HCl, HBr, and $H_3PO_4$, an immobilized acid comprising a sulfonic group on polystyrene, an immobilized acid comprising a copolymer of polystyrene and divinylbenzene, an immobilized acid comprising derivatized silica, and zeolite.

9. The method of claim 7 further comprising the conversion of the HFCA or FFCA into FDCA.

10. The method of claim 9 wherein conversion of the HFCA or FFCA into FDCA comprises oxidation of the HFCA or FFCA.

11. The method of claim 10 wherein the oxidation occurs under acidic conditions.

12. The method of claim 11 wherein the oxidation occurs in the same solvent as the dehydration, and the method does not comprise a step of purifying the HFCA or FFCA.

13. The method of claim 10 wherein the oxidation occurs in the presence of peroxide or oxygen, and the presence of an oxidation catalyst selected from the group consisting of: $CoNO_3/MnNO_3$, Pt/C, Pt—Ru/C, Pd/C, and Pt—Ru/C.

14. The method of claim 13 wherein the oxidation catalyst is Pt—Ru/C.

15. The method of claim 2 wherein the chemical dehydration occurs at a temperature of from 20° C. to about 150° C.

16. A method of synthesizing a 2,5-furan dicarboxylic acid (FDCA) precursor molecule comprising:
performing a chemical dehydration reaction on DHG or an ester thereof, 2KGA or an ester thereof, or 5KGA or an ester thereof, in the presence of a dehydration catalyst, wherein the dehydration catalyst is a basic catalyst;
thereby synthesizing an FDCA precursor molecule selected from the group consisting of FFCA and HFCA.

17. The method of claim 16 wherein the basic catalyst is selected from the group consisting of: $Na_2CO_3$, NaOH, and KOH.

18. The method of claim 17 wherein the reaction is performed in a solvent that is aqueous, organic, or a mixed aqueous/organic solution.

19. The method of claim 16 further comprising the conversion of the HFCA or FFCA into FDCA through oxidation of the HFCA or FFCA.

20. The method of claim 16 wherein the chemical dehydration occurs at a temperature of from 20° C. to about 150° C.

21. The method of claim 1 wherein the dehydration reaction is performed on 2-dehydro-3-deoxy gluconic acid (DHG) or an ester thereof.

22. The method of claim 1 wherein the dehydration reaction is performed on 5-ketogluconic acid (5KGA) or an ester thereof.

23. The method of claim 1 wherein the dehydration reaction is performed on 2-ketogluconic acid (2KGA) or an ester thereof.

24. The method of claim 1 wherein the continuous flow reactor comprises derivatized silica or sand.

25. The method of claim 1 further comprising the conversion of the FFCA or HFCA into FDCA.

* * * * *